(12) United States Patent
Murai et al.

(10) Patent No.: US 6,382,973 B2
(45) Date of Patent: May 7, 2002

(54) DENTAL ROOT CANAL THERAPEUTIC INSTRUMENT

(75) Inventors: Hideyuki Murai; Kanji Matsutani; Toshiyuki Takase, all of Tochigi-ken (JP)

(73) Assignee: Mani, Inc., Tochigi-ken (JP)

( * ) Notice: Subject to any disclaimer, the term of this patent is extended or adjusted under 35 U.S.C. 154(b) by 0 days.

(21) Appl. No.: 09/736,272

(22) Filed: Dec. 15, 2000

(30) Foreign Application Priority Data

Dec. 17, 1999 (JP) .......................................... 11-358917

(51) Int. Cl.[7] ................................................. A61C 5/02
(52) U.S. Cl. ...................................................... 433/102
(58) Field of Search ......................................... 433/102

(56) References Cited

U.S. PATENT DOCUMENTS

| | | | | |
|---|---|---|---|---|
| 1,067,015 A | * | 7/1913 | Fowler | 433/102 |
| 4,260,379 A | * | 4/1981 | Groves et al. | 433/102 |
| 5,882,198 A | * | 3/1999 | Taylor et al. | 433/102 |
| 5,902,106 A | * | 5/1999 | McSpadden | 433/102 |
| 5,984,679 A | * | 11/1999 | Farzin-Nia et al. | 433/102 |

* cited by examiner

Primary Examiner—John J. Wilson
(74) Attorney, Agent, or Firm—Townsend & Banta

(57) ABSTRACT

The present invention relates to a dental root canal therapeutic instrument comprising: a shaft portion and a work portion made of spiral projections in continuation with the shaft portion. A cross section of the projections of the work portion is formed of a set of long sides and a set of short sides and is composed of a parallelogram constituted of a set of acute angle edges and a set of obtuse angle edges, wherein the acute angle edges among the acute angle edges and the obtuse angle edges, which form the projections, are placed on a side of the shaft on the side face of the work portion, and wherein a tip of the acute angle edge is located at a further position with respect to a center axis of the work portion than a position of a tip of the obtuse angle edge.

4 Claims, 11 Drawing Sheets

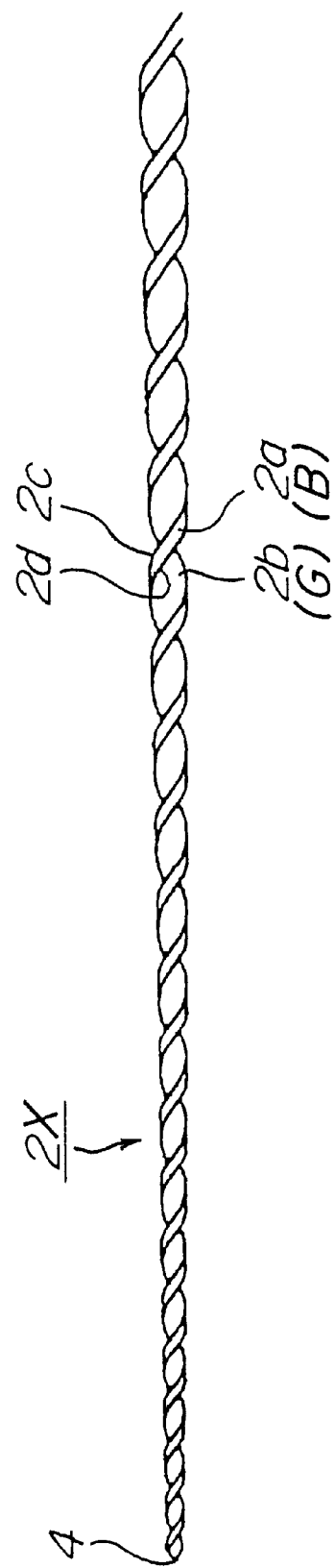
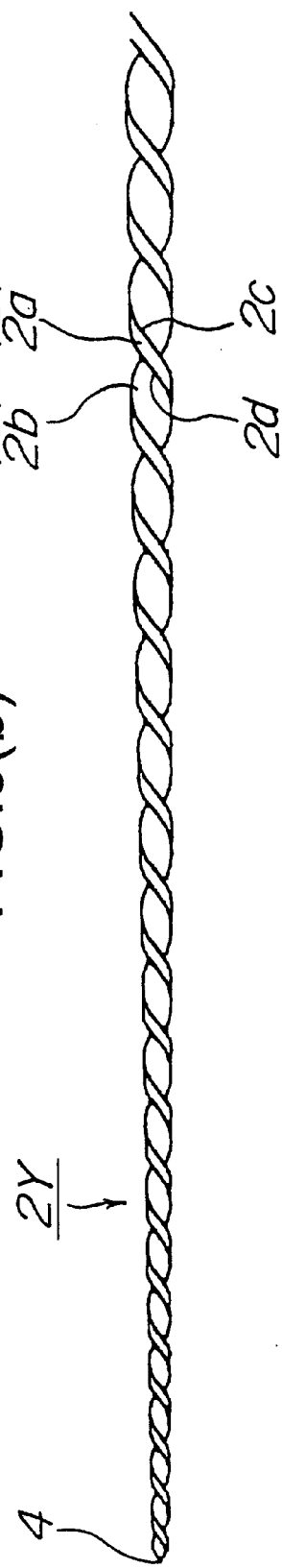

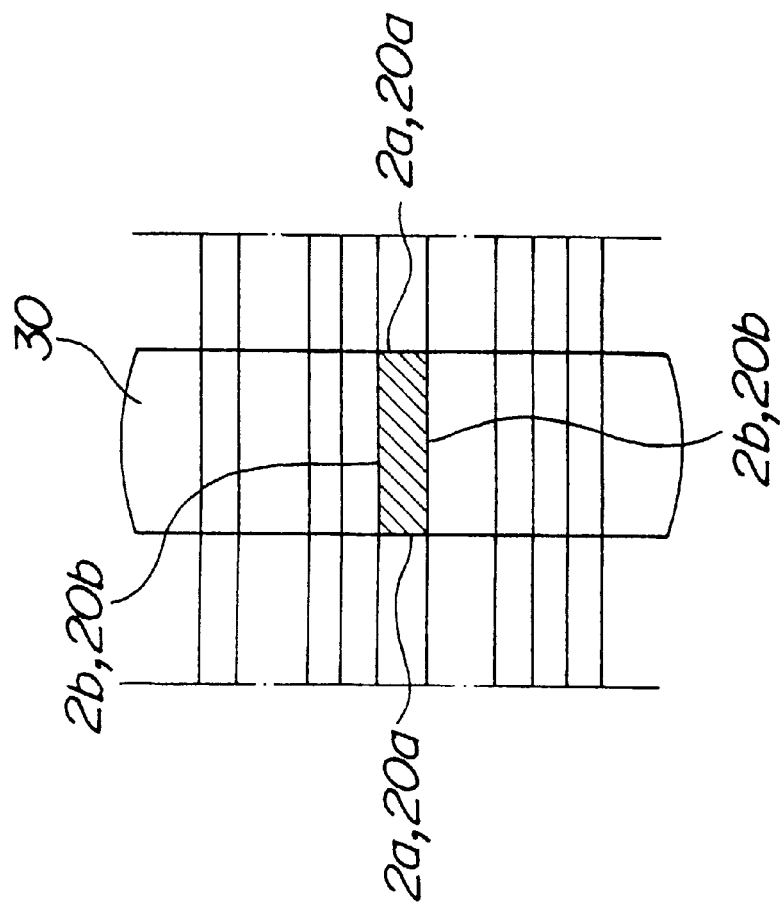
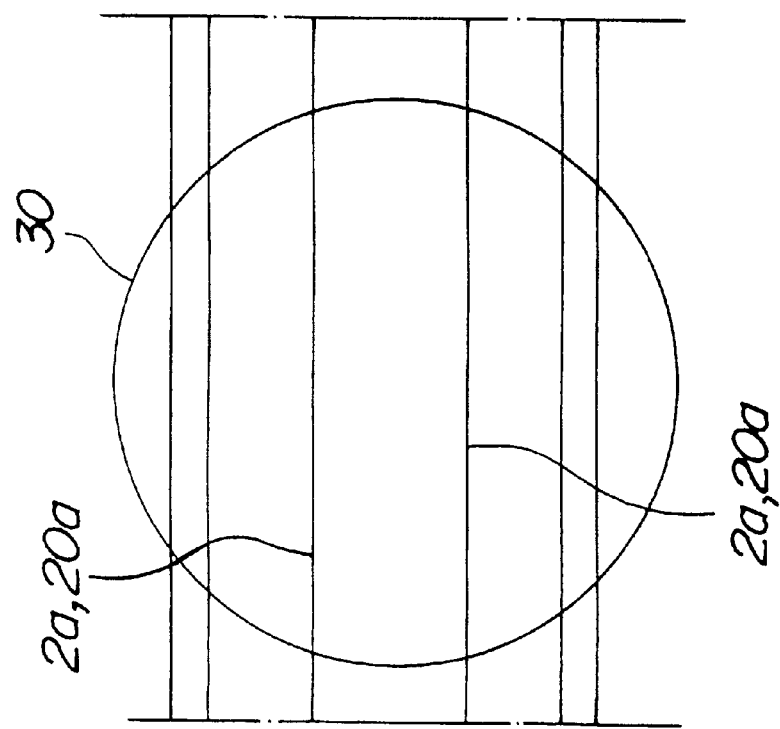

DENTAL ROOT CANAL THERAPEUTIC INSTRUMENT

BACKGROUND OF THE INVENTION

1. Field of the Invention

This invention relates to a dental root canal therapeutic instrument for forming a root canal in dental treatments, such as, so-called, a reamer and a file.

2. Description of Related Art

Root canals in teeth are very fine and have delicately curving shapes, which are greatly different among persons. Reamers and files have been used as therapeutic instruments for grinding and forming such root canals. The reamers and files are grinding instruments having cutting edges extending spirally, and a contour line connecting apexes of the cutting edges is in a tapered shape. The reamers are mainly used for grinding the root canals by rotary manipulation, and the files are mainly used for grinding root canals by pushing and pulling manipulation. There are, among the files, a K-file capable of grinding with rotary motion with a relatively slight torsion angle, an H-file exclusively for pushing and pulling grinding with the greatest torsion angle, and so on.

Now, cross-sectional shapes of work portions of a K-file and an H-file currently provided are described. FIG. 10 is a transversal cross section of a work portion of a K-file; FIG. 11 is a vertical cross section of the work portion. The circles shown in FIG. 10 are circles in inwardly contacting with cutting edges located at an arbitrary position of the file. Numeral 51 in FIG. 10 is a file having a square transversal cross section, whose vertical cross section is shown in FIG. 11. The file 51 among commercially available files has a higher cross-sectional secondary moment. The file 51, therefore, indicates high resistance against bending and torsion but has a small rake θ of the cutting edge 51a, so that the file has inferior grinding ability and removing ability of shavings, and also, has lower tracing ability to root canals. The rake θ means that the perpendicular direction to the moving direction of the cutting edges is zero degree, and it is a minus angle if the rake plane, or the cutting edge plane in the moving direction, is inclined toward the moving direction and a plus angle if toward the opposite direction. The file 51a, accordingly has the rake of a minus angle, and the angle θ is represented as small because the angle is minus with a large absolute value.

Numeral 52 shown in FIG. 10 is a file having triangle transversal cross section. The file has a smaller cross-sectional secondary moment in comparison with the above file 51 and a good tracing ability to the root canals. The file can form a large space between the circle and the surface where the file has a large rake of the cutting edge, so that the file can have good grinding ability and removing ability of shavings.

As a general demand for files, raised are: ability to trace flexibly to any bending shape of root canals, which have large personal differences, good grinding ability, ability to easily remove shavings in accordance with rotary manipulation or pushing and pulling manipulation, good resistance against bending in proper response to the root canal shape or instrument size, high breakdown angle property against torsion, ability not to be locked upon engagement especially during rotation, and so on.

Such a root canal therapeutic instrument can be manufactured by forming a liner material having a diameter corresponding to the targeted size and by twisting the material in adapting a method disclosed in, e.g., Japanese Patent Publication Showa No. 62-22,733 after the outer periphery of the material is formed into a shape with the targeted transversal cross section by slantly grinding in a longitudinal direction by a method disclosed in, e.g., Japanese Patent Publication Showa No. 58-52,782.

The root canal therapeutic instruments, particularly files, grinds the root canal wall according to pushing and pulling manipulation. As shown in FIG. 11, however, the cutting edges in contacting with the root canal wall in the depth direction have approximately the same angles on the pulling side and the pushing side (in a direction along the depth of the root canal, or in a direction along the vertical direction of the file). The file has nearly the same grinding ability in pushing manipulation and in pulling manipulation, so that there raises a problem that the shavings generated along the pushing manipulation may reach a root apex opening and enter into the patient's body. Where the shavings reach the root apex opening and where bacteria thus enter into the human body from the root apex, the bacteria may cause inflammation on the patient, may be accompanied with gross pains, or may cause swellings, and when such a swelling is so severe, the patient may problematically suffer from great pains as his face shape is deformed.

It is an object of the invention to provide a dental root canal therapeutic instrument being flexible, having good grinding ability, and showing grinding ability only during pulling manipulation while not grinding during pushing manipulation, and to provide a manufacturing method for the dental root canal therapeutic instrument.

SUMMARY OF THE INVENTION

To solve the above problems, a dental root canal therapeutic instrument of the invention has a shaft portion and a work portion made of spiral projections in continuation with the shaft portion; the cross section of the work portion is formed of a set of long sides and a set of short sides and is composed of a parallelogram constituted of a set of acute angle edges and a set of obtuse angle edges; the acute angle edges among the acute angle edges and the obtuse angle edges, which form the projections, are placed on a side of the shaft on the side face of the work portion; the tip of the acute angle edge is located at a further position with respect to the center axis of the work portion than the position of the tip of the obtuse angle edge.

Since the transversal cross section of the work portion is the parallelogram, the tip of the acute angle edge is located at a further position with respect to the center axis of the work portion than the position of the tip of the obtuse angle edge. Therefore, when the acute angle edge is made in contact with a targeted circle, the obtuse angle edge is placed without contacting the circle as the apex is located inside the circle. Where the acute angle edge, between the pair of the edges placed in the longitudinal direction at the spirally twisted work portion and placed adjacent to each other, is located on a shaft side, the obtuse angle edge disposed on the tip side of the work portion has an apex lower than the apex of the acute angle edge. Accordingly, even where the acute angle edge contacts with the root canal wall, the obtuse angle does not contact with the root canal wall.

Thus, the root canal wall does contact with the acute angle edge disposed on the shaft side between the two edges placed adjacent to each other, and the edge operates as a cutting edge having a large rake and a good grinding ability during the pulling manipulation, but during the pushing manipulation the edge comes to contact to the wall with a very small rake. Therefore, when the therapeutic instrument is pushed, a portion of the acute edge with a small rake contacts with the root canal wall, and this contact may rub the root canal wall but cannot grind the wall. When the therapeutic instrument is pulled, the root canal wall can be ground in a good state where a portion of the good grinding ability having a large rake comes in contact with the wall.

Therefore, the pushing manipulation of the therapeutic instrument does not produce shavings on the root apex side, so that no shaving is pressed in the direction of the root apex opening.

The above dental root canal therapeutic instrument (hereinafter, referred to as, simply, "therapeutic instrument") may have a ratio of the longer side and shorter side of 1.5 or larger at the transversal cross section of the work portion. With such a structure, the values of the cross-sectional secondary moments are greatly different between in the direction along the longer side and in the direction along the shorter side. Therefore, an arbitrary portion of the work portion may have directionality in bending easiness. Because the work portion is formed in a spirally twisted manner, the work portion as a whole is not subject to the directionality in bending easiness, thereby being capable of providing high flexibility and rigidity.

Moreover, to solve the above problem, a dental root canal therapeutic instrument of the invention has a shaft portion and a work portion made of spiral projections in continuation with the shaft portion; the cross section of the work portion is formed of a rectangular constituted of a set of first edges having keen tips and a set of second edges having rounded tips, located as opposite angle, respectively; the first edges between the first and second edges, which form the projections, are placed on a side of the shaft on the side face of the work portion; the tip of the first edge is located at a further position with respect to the center axis of the work portion than the position of the tip of the second edge.

Where the cross section of the work portion is set to such a rectangular, only the first edge located on the shaft side may operate as a cutting edge by rendering the distance from the central axis to the second edge shorter than the distance to the first edge by rounding the tip of the second edge.

BRIEF DESCRIPTION OF THE DRAWINGS

The above and other objects and features of the invention are apparent to those skilled in the art from the following preferred embodiments thereof when considered in conjunction with the accompanied drawings, in which:

FIG. 5 is an illustration showing a twisting direction at the work portion;

FIG. 8 is an illustration for showing a method for manufacturing the therapeutic instrument;

DETAILED DESCRIPTION OF THE PREFERRED EMBODIMENTS

Figure 1A:
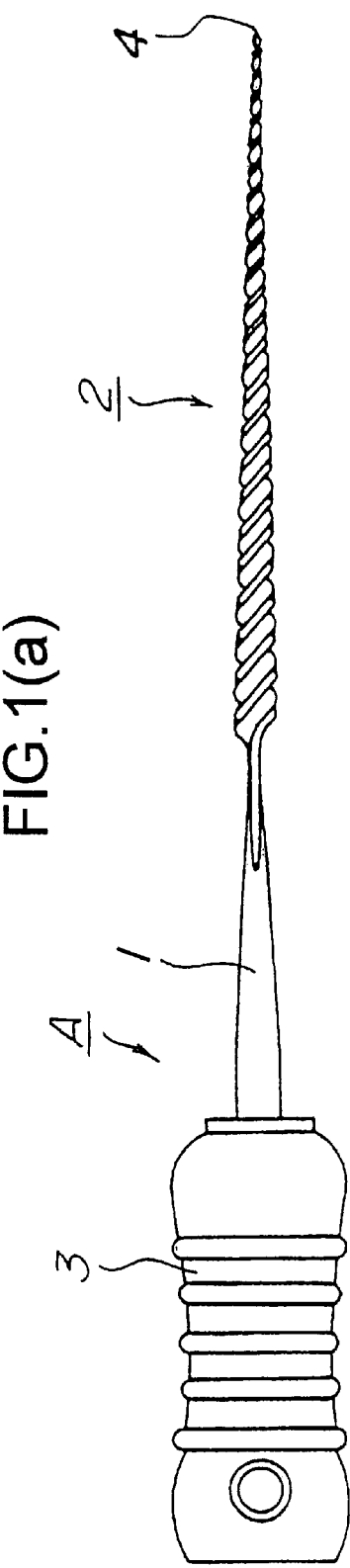
FIG. 1 is a side view illustrating the whole structure of the therapeutic instrument.

Referring to the drawings, preferred embodiments of the invented therapeutic instrument are described below.

The therapeutic instrument A is a tool for forming a root canal wall of a tooth upon grinding the root canal wall and is specially manipulated by a doctor with control of his grip. The therapeutic instrument A is generally available in plural kinds of sizes in a range of #06 (tip diameter 0.06 mm) to #140 (tip diameter 1.40 mm).

The therapeutic instrument A grinds the root canal to form it by doctor's manipulation in reliance with delicate sense on finger tips, which clamp the therapeutic instrument A. According to grinding manipulation, the therapeutic instrument A is replaced with a larger size therapeutic instrument A as the diameter of the root canal is more enlarged, and the therapeutic instrument A is used by further manipulation to form the root canal in the patient's tooth to have targeted diameter and shape.

The therapeutic instrument A is constituted of a shaft portion 1, and a work portion 2 in continuation with the shaft portion 1. In this embodiment, a tip 4 of the work portion 2 is made of an apex of a prescribed angle (e.g., 60 to 90 degrees) notwithstanding of the size and the cross-sectional shape of the work portion 2.

The shaft portion 1 is attached to a synthetic resin handle 3 by an insertion molding as to form a united body during the series of the manufacturing steps.

The cross section of the shaft portion 1 is formed to be from a circle to a parallelogram serving as a cross section of the work portion as coming closer to the work portion 2 from the side of the handle 3. With such a structure of the work portion 2, the therapeutic instrument can eliminate stress integration without abruptly changing the cross-sectional shape and area and can oppose well to bending force exerted during therapy periods.

The work portion 2 has a stick type shape with a spiral structure in which a linearly extending body having a parallelogram cross section is twisted in prescribed direction and angle. The whole contour of the work portion 2 is straight or tapered shape, which is shown in the drawings.

The work portion 2 has the cross section in the parallelogram shape with short sides 2a and long sides 2b. The length of the long sides 2b is set 1.5 times or more of the length of the short side 2a. The ratio of the long side 2b and the short side 2a is determined in taking many doctors' views as a ratio showing apparent superiority over other ratios in terms of flexibility, tracing ability in curing root canals, and visual novelty, in comparison with conventional products. The upper limit of the ratio is 1.5 preferably. This is based on opinions from doctors on sites, in which a file is too flexible, lacks grinding ability, and is useless if the ratio is more than 1.5.

The cross section of the work portion 2 is thus formed in the parallelogram, and the acute angle edge 2c and the obtuse angle edge 2d are formed on opposite angle lines. The acute angle edge 2c contacts with a circle to which the work portion 2 contacts inwardly and operates as a cutting edge.

The obtuse angle edge 2d does not contact with the circle and does not operate as a cutting edge.

Figure 2B:
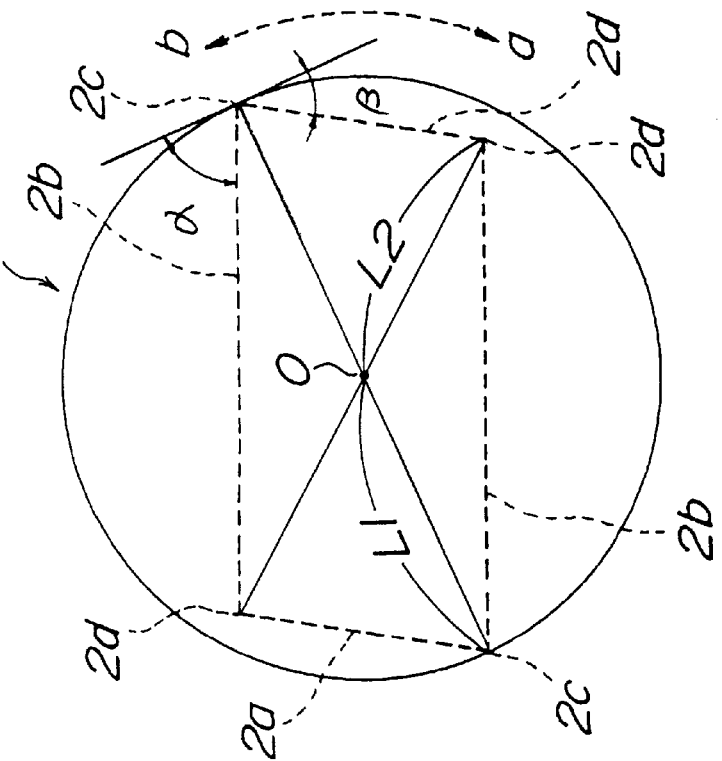
FIG. 2 is a transversal cross section of a work portion of a therapeutic instrument according to a first embodiment.
Figure 2A:
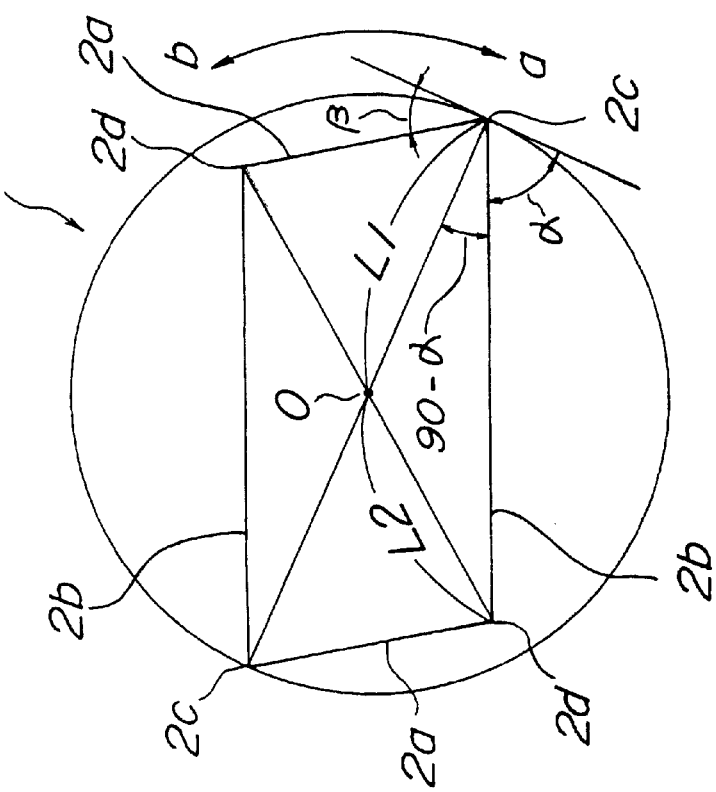

As shown in FIGS. 2(a), 2(b), relationship between the distance L1 from the central axis O to the acute angle edge 2c and the distance L2 from the central axis O to the obtuse angle edge 2s is L1>L2. That is, the distance from the central axis O to the tip of the acute angle edge 2c is relatively long whereas the distance from the central axis O to the tip of the obtuse angle edge 2d is relatively short.

The work portion 2 is formed by twisting an axial material having a parallelogram cross section, and the acute angle edge 2c serving always as a cutting edge is formed on a shaft side by twisting the material from the obtuse angle edge 2d side of one short side 2a to the acute angle edge 2c of the same short side 2a. The short side 2a of the parallelogram cross section becomes a projection B; the long side 2b of the parallelogram cross section becomes a flute G. Those projections B and flutes G appear alternatively on sides of the work portion 2 (see, FIG. 5).

An angle α formed between the long side 2b constituting the acute angle edge 2c (cutting edge 2c) and the circle becomes larger, and an angle β formed between the short side 2a constituting the acute angle edge 2c and the circle becomes smaller. Therefore, as shown in FIG. 2(a), the work portion 2 proceeds in a direction of arrow a, the angle (90−α) operates as a rake, and the angle β operates as a clearance angle. That is, the cutting edge 2c presents good cutting functions when the cutting edge 2c contacts to the root canal wall and proceeds in a direction of the long side 2b. The cross section of the work portion 2 has a directionality according to which direction the acute angle edge 2c and the obtuse angle edge 2d are placed, and the cutting ability can be designed by synthesizing the positions of the acute angle edge 2c and the obtuse angle edge 2d and the twisting direction.

For example, where the cross section of the work portion 2 as shown in FIG. 2 is supposedly a shape when seen from a side of the shaft portion 1, the therapeutic instrument has a good cutting ability when the acute angle edge 2c proceeds in the direction of arrow a in the case where the acute angle edge 2c is formed on a right side of the short side 2a and the obtuse angle edge 2d is formed on a left side of the short side 2a as seen from the central axis O (work portion 2X). Where the targeted therapeutic instrument A is structured as a reamer, the acute angle edge 2c can be proceeded in the direction of arrow a by simply rotating the therapeutic instrument A in the direction of arrow a.

However, where the targeted therapeutic instrument A is structured as a file, the therapeutic instrument A is required to be twisted so that the acute angle edge 2c proceeds correlatively in the direction of arrow a according to the manipulating of either pulling or pushing. Particularly, it is required to set the twisting direction at the work portion 2X to be the right direction when seen from the shaft side as shown in FIG. 5(a) to provide good cutting ability when the therapeutic instrument A is pulled. In such a case, where the therapeutic instrument A is manipulated as pulled, the acute angle edge 2c (cutting edge 2c), apparently, rotates in the direction of arrow a according to the extending direction of the acute angle edge 2c (cutting edge 2c). Where the therapeutic instrument A is manipulated in a pushing manner, the acute angle edge 2c is retarded in the direction of arrow b, and because the angle β is small, the acute angle edge 2c provides with little cutting ability.

As shown in FIG. 2(b), when seen from the central axis a, the therapeutic instrument has a good cutting ability when the acute angle edge 2c proceeds in the direction of arrow b in the case where the acute angle edge 2c is formed on a left side of the short side 2a and the obtuse angle edge 2d is formed on a right side of the short side 2a as seen from the central axis O (work portion 2Y). Where the targeted therapeutic instrument A is structured as a file and produces good cutting ability when manipulated in a pulling manner, the twisting direction of the work portion 2Y is required to be in the left direction as shown in FIG. 5(b). In this case, by pulling manipulation of the therapeutic instrument A, the acute angle edge 2c (cutting edge 2c), apparently, rotates in the direction of arrow b according to the extending direction of the acute angle edge 2c (cutting edge 2c). Moreover, when the therapeutic instrument A is manipulated in a pushed manner, the acute angle edge 2c is retarded in the direction of arrow a, and because the angle β is small, the acute angle edge 2c provides with little cutting ability and is made back in sliding on the contact surface.

Figure 3:
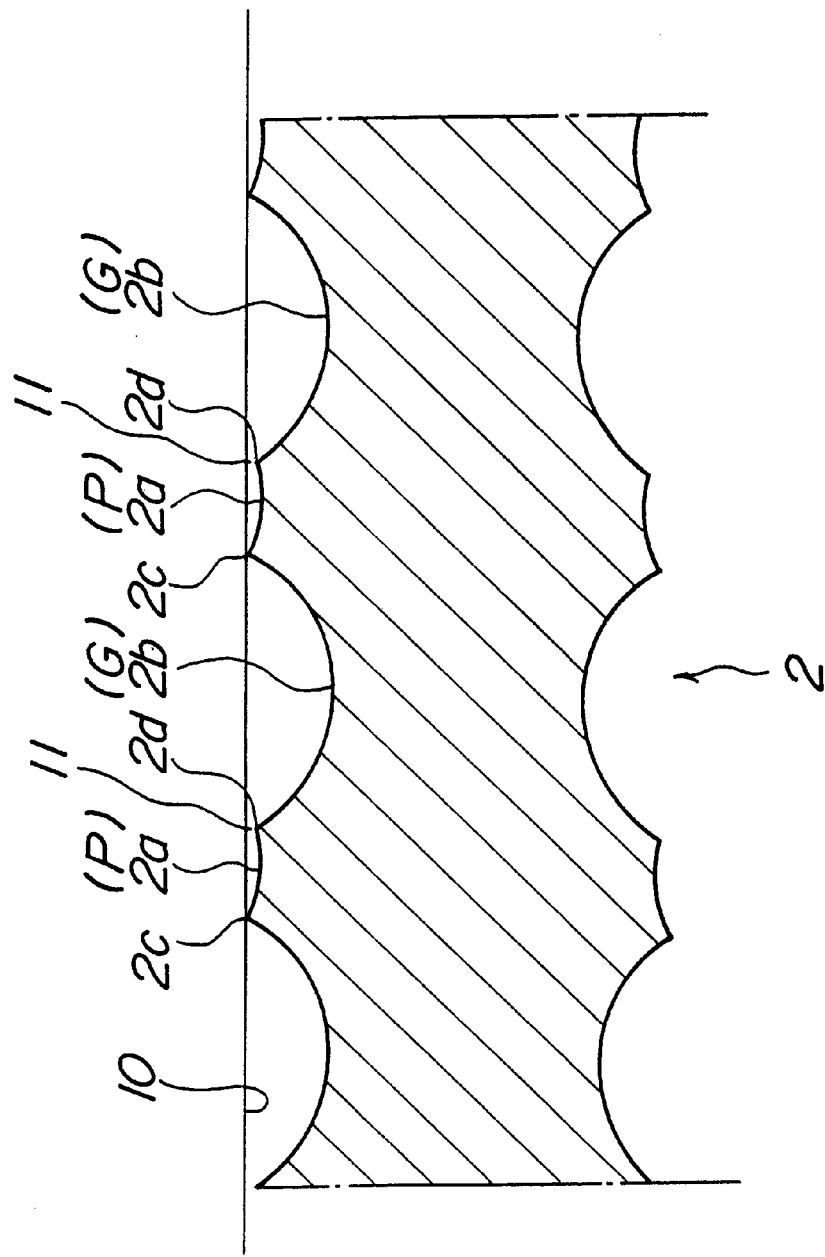
FIG. 3 is a vertical cross section of the therapeutic instrument according to the first embodiment.

FIG. 3 is a vertical cross section in the longitudinal direction of the work portion 2X shown in FIG. 2(a) and FIG. 5(a). The twisted angle of the work portion shown in FIG. 3 is 43 degrees. As shown in FIG. 3, the projections B formed of the short side 2a and the flutes G formed of the long sides 2b are disposed alternatively. In the vertical cross section in the longitudinal direction of the work portion 2, the acute angle edge 2c between the acute angle edge 2c and the obtuse angle edge 2d, which constitute the projections B, projects more outwardly than the obtuse angle edge 2c. The work portion 2Y shown in FIG. 2(a) and FIG. 5(a) also has substantially the same transversal cross section as that of the work portion 2X.

Figure 4:
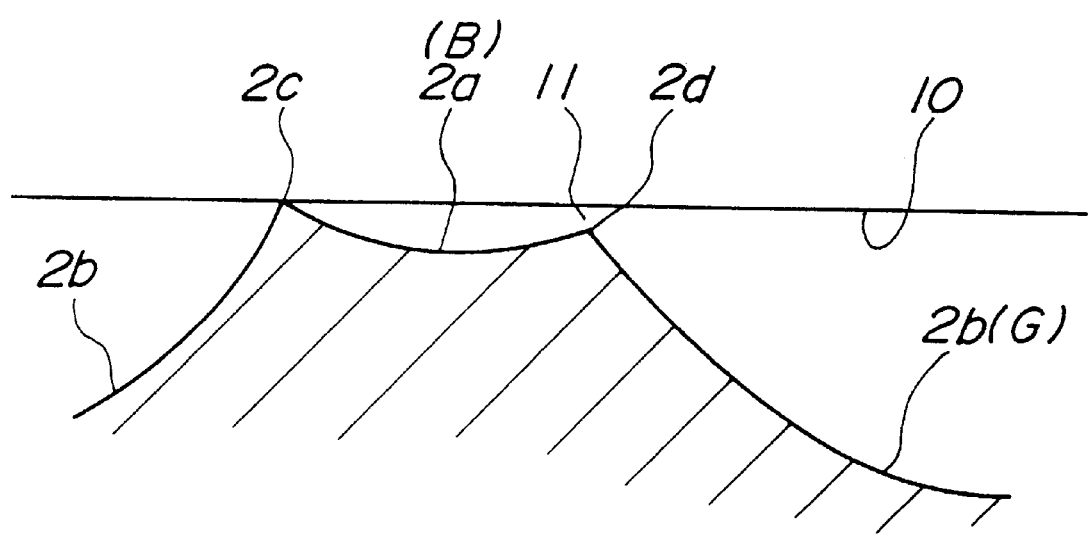
FIG. 4 is an enlarged view illustrating relationship between two edges located adjacently to each other in a longitudinal direction and a root canal wall.

In FIG. 3, the apexes of the acute angle edge (cutting edge) 2c are connected with a line 10, the apexes of the obtuse angle edge (cutting edge) 2d are isolated without contacting to the line 10. At that time, the size of the gap 11 (see, FIG. 4) from the line 10 to the apex of the obtuse angle edge 2d changes according to the conditions such as the angle of the acute angle edge 2c and the length of the short side 2a.

It is to be noted that the line 10 connecting the apexes of the cutting edge 2c corresponds to the root canal wall when the root canal is subject to therapy with the therapeutic instrument A. That is, the invented therapeutic instrument A is used for actual therapy, the acute angle edge 2c contacting with the root canal wall of the patient provides mainly the cutting ability.

With the therapeutic instrument A thus structured, the angle range of the acute angle edge 2c in the transversal cross section of the work portion 2 is preferably in a range between 80 degrees and 87 degrees. Therefore, the angle range of the obtuse angle edge 2d is between 93 degrees and 100 degrees.

As described above, the work portion 2 of the therapeutic instrument A is very fine (the largest diameter (size of opposite angle line between the acute angle edges 2c) of the tip portion is, #140, 1.40 mm), and very delicate work is required, where a prescribed clearance is set.

By setting the upper limit of the acute angle edge 2c to 87 degrees, the parallelogram in the cross section of the work portion 2 can be surely guaranteed. That is, the acute angle edge can be set easily and can be surely guaranteed even where the therapeutic instrument A is subject to deviations within the range of the fabrication clearance as set in the manufacturing process.

By setting the lower limit of the acute angle edge 2c to 80 degrees, the therapeutic instrument can ensure the durability of the acute angle edge 2c as a cutting edge and can prevent the acute angle edge 2c from serving as the cutting edge during the pushing manipulation. That is, where the angle of the acute angle edge 2c is set at 80 degrees or less, the acute angle edge 2c loses rigidity as the cutting edge, and such an angle is disadvantageous in terms of strength.

Where the acute angle edge 2c is set at 80 degrees or less, the angle p shown in FIG. 2(a) becomes larger, and when the therapeutic instrument is retarded in the direction of arrow b, the acute angle edge 2c can serve as a cutting edge to grind the root canal wall. Therefore, when the therapeutic instrument A is manipulated in a pushing manner, the therapeutic instrument can show the cutting ability, so that the shavings generated along the pushing manipulation may reach the root apex opening. Thus, even where the acute angle edge 2c operates as a cutting edge in the pushing manipulation, the angle β is not so large as the angle α, and consequently, the acute angle edge 2c grinds the root canal wall and slides on the wall and becomes worn in losing the cutting ability at a time of the pulling manipulation due to dullness of the acute angle edge 2c.

Accordingly, the acute angle edge 2c is preferably set in a range of 87 degrees as the upper limit and 80 degrees as the lower limit.

With the therapeutic instrument A having the work portion 2 thus formed, the acute angle edge, or the cutting edge 2c, does not show the cutting ability during the pushing manipulation, but show the cutting ability during the pulling manipulation. Particularly, since the cutting edge 2c is the acute angle, the edge contacts at a larger angle with the root canal wall, so that the edge can show the good cutting ability in engaging with the root canal wall.

Figure 6:
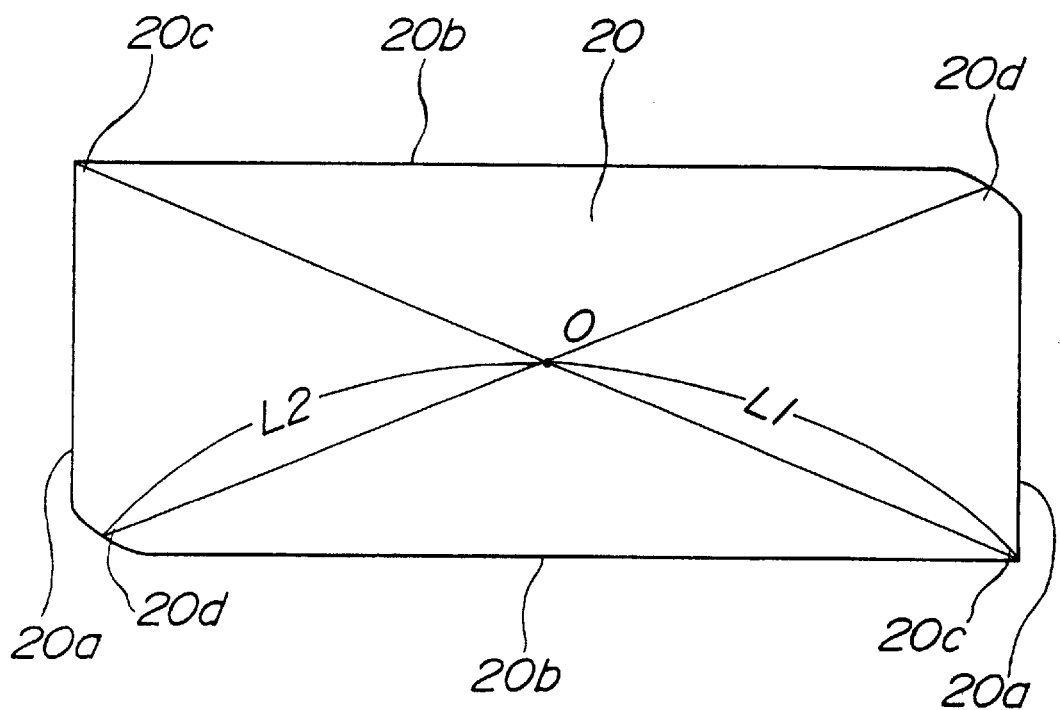
FIG. 6 is a transversal cross section showing a therapeutic instrument according to a second embodiment.
Figure 7:
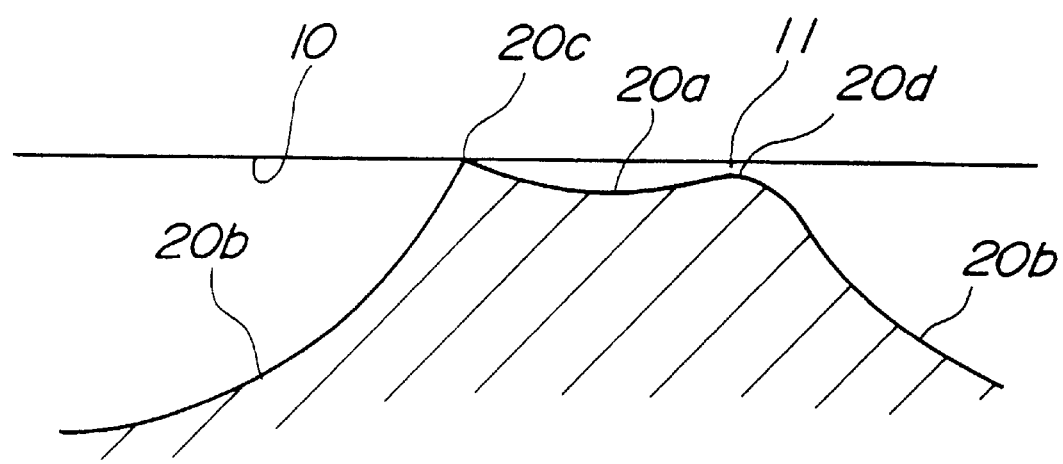
FIG. 7 is an enlarged view illustrating relationship between two edges located adjacently to each other in a longitudinal direction and a root canal wall in the therapeutic instrument according to the second embodiment.

Referring to FIG. 6 and FIG. 7, a structure of the second embodiment of a work portion 2 in the therapeutic instrument A is described next. The work portion 2 in this embodiment is structured with a cross section 20 shown in FIG. 6. This cross section 20 is formed as a parallelogram including a rectangular made of short sides 20a and long sides 20b, and the length of the long side 20b is designed 1.5 times or more of the length of the short side 20a.

In this embodiment, the cross section 20 is formed in a rectangular, and an edge 20 and a chamfered edge 20d are formed astride the short side 20a. The respective edges 20c, 20d are designed to have an intersecting angle of 90 degrees between the short side 20a and the long side 20b, and the edge 20c is made by intersecting the sides 20a, 20b as an edge, whereas the chamfered edge 20d is made by chamfering the apex intersecting the sides 20a, 20b and the vicinity of the apex by grinding or plastic fabrication.

With the cross section 20, the distance from the center O to the edge 20c is larger than the distance from the center O to the surface of the chamfered edge 20d. The cross section 20 produces directionality in the same way as in the first embodiment by forming the chamfered edge 20d. When the cross section 20, or the work portion, is twisted, therefore, the twisting direction is determined in corresponding to the position of the edge 20c when seen from the shaft portion 1 side. At that time, the relation between the position of the edge 20c and the twisting direction is substantially the same as that in the first embodiment.

Where the work portion 2 is made by twisting a material having the cross section 20 with a prescribed angle, a gap 11 is formed between the chamfered edge 20d and the line 10 when the edges 20c at the work portion 2 are connected with the line 10 as shown in FIG. 7.

However, the chamfered shape and chamfered size of the chamfered edge 20d are not specifically limited and can be set properly in accordance with the nature of the targeted therapeutic instrument A. One angle of the parallelogram in this embodiment is preferably set to 80 to 90 degrees because the edge loses its durability if equal to or less than 80 degrees.

The therapeutic instrument A having such a work portion 2 can provide, in substantially the same way as that in the first embodiment, good cutting ability in the pulling manipulation but little cutting ability in the pushing manipulation.

Figure 9:
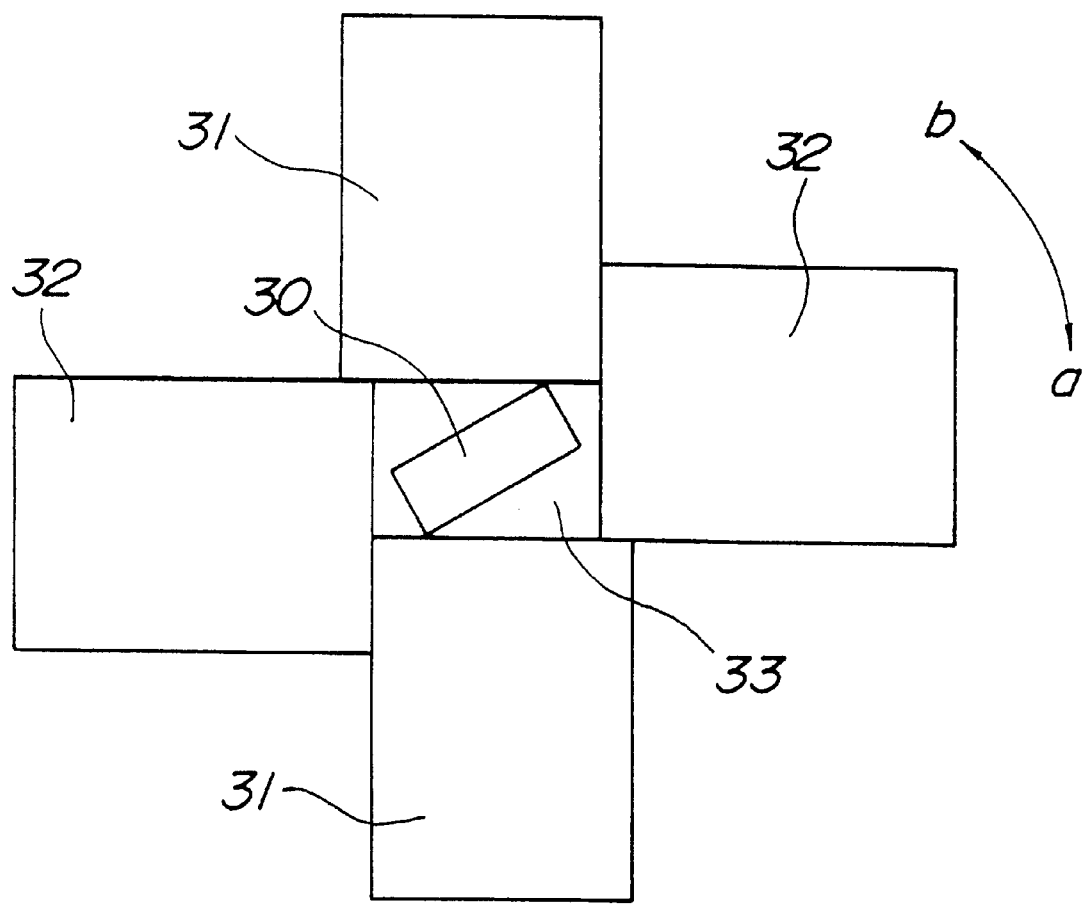
FIG. 9 is an illustration for showing a method for twisting the work portion.
Figure 10:
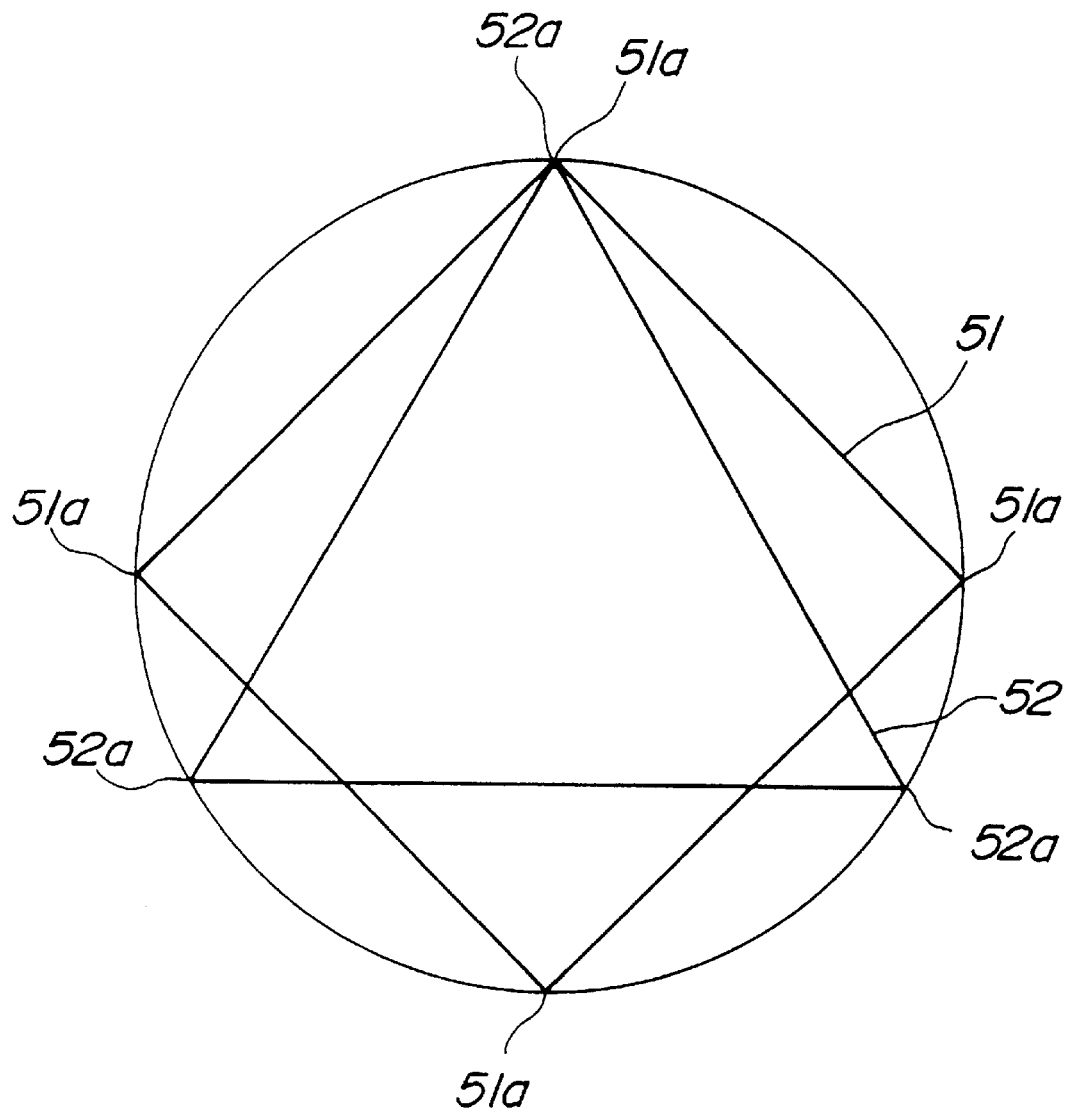
FIG. 10 is a view showing a transversal cross section of a conventional file.
Figure 11:
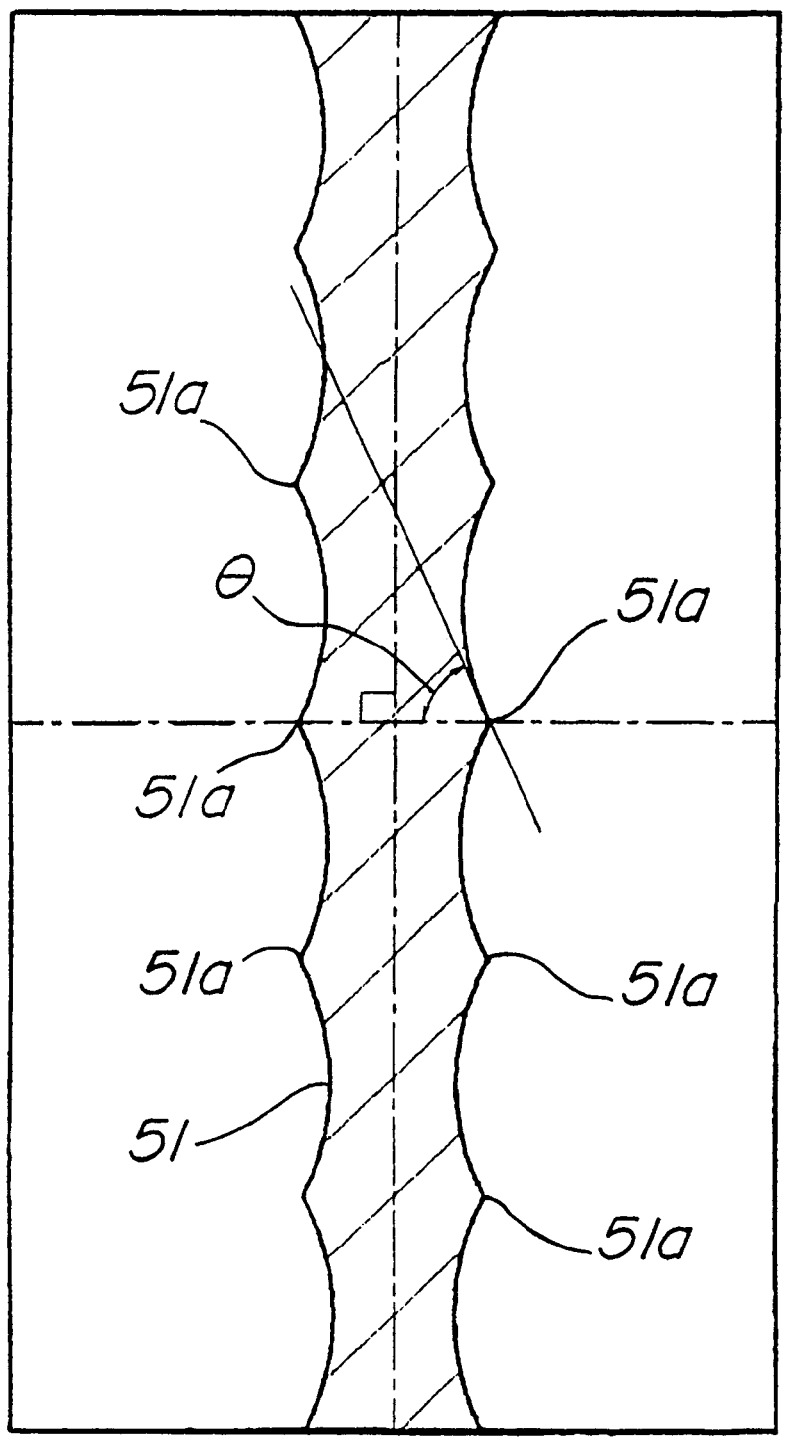
FIG. 11 is a view showing a vertical cross section of a conventional file.

Referring to FIG. 8 and FIG. 9, an example of a method for manufacturing the therapeutic instrument A is described next. This method is particularly for making the work portion 2, and this is not questioning whether the work portion 2 is united with a handle for hand or finger 3 made of synthetic resin after the work portion 2 is formed in connection with the shaft portion 1 or whether the therapeutic instrument A is connected to a handle for engine to be mounted to a handpiece or is attached directly to another jig without using any handle.

In FIG. 8, numeral 30 in an illustration (a) is a material, whose diameter is determined generally in accordance with a size of the end on the shank side of the work portion. Numeral 30 in an illustration (b) is an intermediate material, which is formed through grinding step or the like performed in advance with a portion corresponding to the shaft portion 1 and with a portion corresponding to the work portion 2 having diameter and taper corresponding to the size of the targeted therapeutic instrument A. The material constituting the intermediate material 30 is formed of a material free from rust and not requiring any thermal treatment, for example, an austenite based stainless steel showing adequately high hardness and strength against bending by cool-drawing.

The intermediate material 30 is ground with a hone in pressing the material by a pressing metal as disclosed in e.g., Japanese Patent Publication No. 58-52,782. The first step of this grinding is, as shown in FIG. 8(a), to furnish the work portion 2 with sizes of the long sides 2b, 20b by grinding the material from two parallel directions, thereby furnishing the faces of the short sides 2a, 20a by this step.

Subsequently, the intermediate material 30 is rotated as shown in FIG. 8(b). By setting the rotary angle, the acute angle edge 2c in the first embodiment is set in a range of 80 degrees to 87 degrees, or to the right angle as in the second embodiment. FIG. 8(b) shows a case that the intermediate material 30 is rotated by 90 degrees to form the cross section 20 of the second embodiment.

After the intermediate material 30 is rotated through the first step, the work portion 2 can be furnished with the targeted cross section 2, 20 by grinding the material in two parallel directions to form the sizes of the short sides 2a, 20a and thereby to furnish the long sides 2b, 20b. The meaning of "furnishing" herein means "formation."

After the intermediate material 30 is ground into a linear shape having the targeted cross section in a manner as described above, the therapeutic instrument A is structured to have the targeted work portion 2 by twisting the material with a prescribed twisting angle.

When the intermediate material 30 is twisted, it is possible to adapt a method disclosed in Japanese Patent Publication No. 62-22,733. Particularly, to form a work portion 2 according to the second embodiment by twisting the intermediate material 30 having the cross section 20, it is preferable to adapt a method shown in FIG. 9.

In the method shown in FIG. 9, a pair of needle pressing jigs 31 and a pair of needle supporting jigs 32 are disposed as opposed to each other with predetermined intervals, and the intermediate material 30 is inserted into a molding space 33 made of those needle pressing jigs 31 and those needle supporting jigs 32. The intermediate material 30 is twisted under this state by rotating the entire structure, and at the same time, by pressing the needle pressing jigs 31 to the edges of the intermediate material 30, the edge can be chambered.

Accordingly, by using the method shown in FIG. 9, the work portion 2 of the second embodiment having the chamfered edge 20d can be manufactured through one twisting step. FIG. 9 is a cross section when seen from the shaft side.

In the case where the work portion 2 of the second embodiment is manufactured by rotating the needle pressing jigs 31 and the needle supporting jigs 32 as a united body, when the twisting direction of the targeted work portion 2 is the right direction, the jigs 31, 32 are to be moved from the shaft side to the tip side of the intermediate material 30 in rotating in the direction of arrow a in FIG. 9, and when the twisting direction of the targeted work portion 2 is the left direction, the jigs 31, 32 are to be moved from the shaft side to the tip side in rotating in the direction of arrow b in FIG. 9.

By implementing the above manufacturing method, the work portion 2 can be reasonably produced having the parallelogram cross section in which the length of long sides 2b, 20b are set 1.5 time or more of the length of the short sides 2a, 20a. After the short side faces and the long side faces are finished, the material is twisted with a prescribed twisting angle. The manufacturing method of the invention optionally includes, after the twisting step, surface furnishing steps such as a deburring step, a surface acid-rinsing step, a surface hardening step, a surface coloring step, and so on.

It is to be noted that in the work portion 2 according to the respective embodiments, it is preferable to design that the rate of the long side to the short side is made larger as coming closer to the shaft portion 1. In such a case, though the work portion 2 may have a larger diameter as closer to the shaft portion 1, the therapeutic instrument A can maintain the flexibility by rendering larger the rate. It is also preferable to set larger the rate, as the side of the therapeutic instrument A is larger. In this case, the therapeutic instrument A can maintain the flexibility notwithstanding the work portion 2 having a larger diameter as the size increases.

It is further preferable to set larger ratio between the rate of the long side to the short side on a side of the shaft portion 1 at the work portion 2 and the rate on a side of the tip portion as the size of the therapeutic instrument increases. It is also preferable to set the ratio larger as the work portion 2 has a larger tapered portion. With this ratio, the therapeutic instrument A can maintain the flexibility of the work portion 2.

The twisting angle of the work portion 2 is not limited. Particularly, when a doctor controls with his hands, it is preferable to design the angle to be 40 degrees or more and around 30 degrees in the range of approximately 5 mm from the tip. By setting the twisting angle of the tip portion to 30 degrees, it is possible to change the cutting ability between this portion and the portion following this portion.

In the respective embodiments, the cross section of the work portion 2 is defined as a parallelogram or a parallelogram including a rectangular, but those shapes are not needed to be strictly a parallelogram or a rectangular, and any shapes can be useful as far as those are roughly a parallelogram or a rectangular.

Figure 1B:
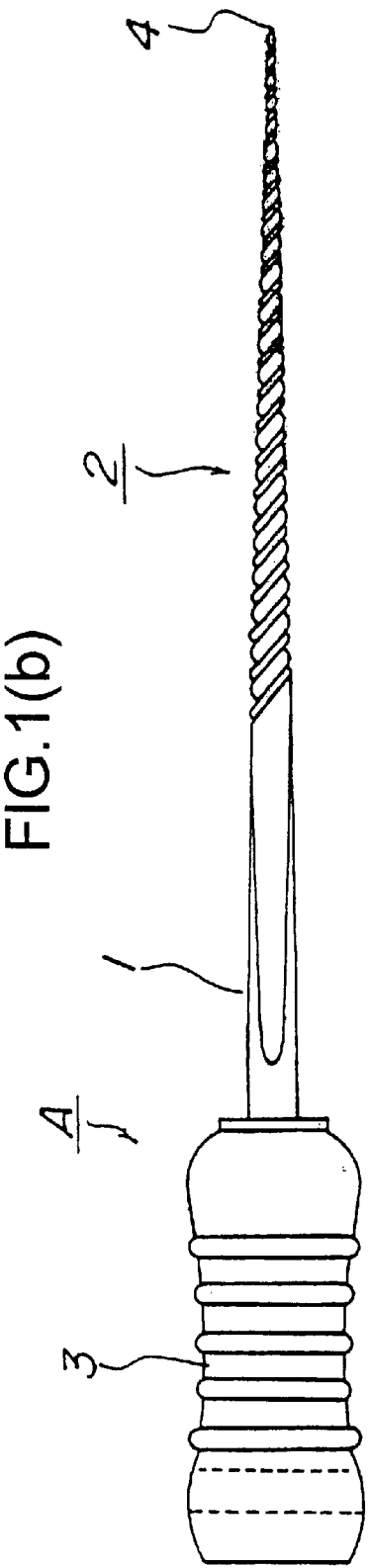

The handle attaching the shaft portion 1 can be the handle 3 shown in FIG. 1 where the handle is controlled mainly by hands. Where the therapeutic instrument A is mounted for therapeutic use, a metal handle for engine may be used. It is preferable to set the twisting angle to be 30 degrees or lower at the work portion 2, which is intended to be mounted for handpiece. If the twisting angle is so large, the edges engage much more with the root canal wall by rotation of the handpiece.

As described above, the therapeutic instrument according to the invention prevents the edges from showing cutting ability during the pushing manipulation and allows showing the cutting ability only during the pulling manipulation. Therefore, when it is used for root canal therapy, no shaving is generated on a side of root apexes, so that no shaving reaches the root apexes.

Where the cross section of the work portion is designed to be a parallelogram or a parallelogram including a rectangular, the therapeutic instrument A shows a high flexibility.

By forming one edge of the two edges placed adjacent to each other in the longitudinal direction to be chamfered and setting the chamfered edges lower than the other edges, the chamfered edges do not show the cutting ability, so that the therapeutic instrument can show the cutting ability only during the pulling manipulation.

With the manufacturing method according to the invention, a therapeutic instrument can be reasonably manufactured having the cross section of parallelogram or a parallelogram including a rectangular.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention should not be limited by the specification, but should be defined claims set forth below.

What is claimed is:

1. A dental root canal therapeutic instrument comprising:

a shaft portion; and a work portion made of spiral projections having a cross section in continuation with the shaft portion, wherein the cross section of said spiral projections of the work portion is comprised of a set of long sides and a set of short sides which form a parallelogram having a set of acute angle edges formed on a side of said shaft portion on a side face of said spiral projections with tips operating as cutting edge and a set of obtuse angle edges with tips, said acute angle edge tips being disposed further from a center axis of the work portion than said obtuse angle edge tips;

said acute angle edges having an angle range of between 80 and 87 degrees, and said obtuse angles edges having an angle range of between 93 and 100 degrees.

2. The dental root canal therapeutic instrument according to claim 1, wherein the long sides of the parallelogram-shaped cross section are at least 1.5 times as long as the short sides.

3. A dental root canal therapeutic instrument comprising:
a shaft portion; and
a work portion made of spiral projections having a cross section in continuation with the shaft portion,
wherein the cross section of the work portion forms a rectangle having a set of first edges with keen tips and a set of second edges with rounded tips, said first edges forming projections located opposite said second edges, the first edges being placed on a side of the shaft on a side face of the work portion, and the tips of the first edges being located further from a center axis of the work portion than the tips of the second edges.

4. The dental root canal therapeutic instrument according to claim 3, wherein the long sides of the rectangular cross section of the work portion are at least 1.5 times as long as the short sides.

* * * * *